United States Patent
Brenner et al.

(10) Patent No.: US 6,231,956 B1
(45) Date of Patent: May 15, 2001

(54) WEAR-RESISTANCE EDGE LAYER STRUCTURE FOR TITANIUM OR ITS ALLOYS WHICH CAN BE SUBJECTED TO A HIGH MECHANICAL LOAD AND HAS A LOW COEFFICIENT OF FRICTION, AND METHOD OF PRODUCING THE SAME

(75) Inventors: Berndt Brenner, Pappritz; Steffen Bonss, Zella-Mehlis; Hans-Joachim Scheibe, Dresden; Holger Ziegele, Lorch, all of (DE)

(73) Assignee: Fraunhofer-Gesellschaft zur Förderung der angewandten Forschung e. V, München (DE)

( * ) Notice: Subject to any disclaimer, the term of this patent is extended or adjusted under 35 U.S.C. 154(b) by 0 days.

(21) Appl. No.: 09/147,810

(22) PCT Filed: Sep. 12, 1997

(86) PCT No.: PCT/DE97/02071

§ 371 Date: Jun. 14, 1999

§ 102(e) Date: Jun. 14, 1999

(87) PCT Pub. No.: WO98/11272

PCT Pub. Date: May 19, 1998

(30) Foreign Application Priority Data

Sep. 13, 1996 (DE) .............................. 196 37 450

(51) Int. Cl.⁷ .............................. B32B 9/00; C23C 26/00
(52) U.S. Cl. .......................... 428/216; 427/457; 427/470; 427/532; 427/534; 427/540; 427/577; 428/212; 428/336; 428/408; 428/457
(58) Field of Search .................................. 428/212, 408, 428/216, 336, 457; 427/457, 470, 532, 534, 540, 577

(56) References Cited

U.S. PATENT DOCUMENTS

| 4,511,411 | 4/1985 | Brunner et al. . |
| 4,692,385 | 9/1987 | Johnson . |

(List continued on next page.)

FOREIGN PATENT DOCUMENTS

| 3917211 | 11/1990 | (DE) . |
| 0105835 | 4/1984 | (EP) . |

(List continued on next page.)

OTHER PUBLICATIONS

Brenner et al., "Mechanical and Tribological Properties of Laser Gas Ti6A14V", pp. 477–484, presented at the ECLAT '96 (6th European Conference on Laser Treatment of Materials) (Sep. 16–18, 1996).

(List continued on next page.)

*Primary Examiner*—Archene Turner
(74) *Attorney, Agent, or Firm*—Greenblum & Bernstein, P.L.C.

(57) ABSTRACT

Wear-resistant edge layer for titanium and its alloys which can be subjected to high loads and has a low coefficient of friction. The wear-resistant edge layer includes a hard amorphous carbon layer, an intermediate layer, and a laser gas alloyed layer. The wear-resistant edge layer may include a 200 to 400 nm thick hard amorphous carbon layer, a 50 to 200 nm thick intermediate layer, and a 0.3 to 2.0 mm thick laser gas alloyed layer. The laser gas alloyed layer may include precipitated titanium nitride needles and have a hardness between 600 HV0.1 and 1400 HV0.1. Process for producing a wear resistant edge layer on a substrate. The process includes forming a laser gas alloyed layer by melting a surface of a substrate, applying an intermediate layer by Laser-Arc, and depositing a hard amorphous carbon layer on the intermediate layer by Laser-Arc.

35 Claims, 2 Drawing Sheets

U.S. PATENT DOCUMENTS

| | | |
|---|---|---|
| 4,902,359 | 2/1990 | Takeuchi et al. . |
| 4,902,535 | 2/1990 | Garg et al. . |
| 5,009,966 | 4/1991 | Garg et al. . |
| 5,260,107 | 11/1993 | Kawamura et al. . |
| 5,326,362 | 7/1994 | Shetty et al. . |
| 5,366,345 | 11/1994 | Gerdes et al. . |
| 5,368,939 | 11/1994 | Kawamura et al. . |
| 5,413,641 | 5/1995 | Coulon . |
| 5,593,719 | 1/1997 | Dearnaley et al. . |
| 5,605,714 | 2/1997 | Dearnaley et al. . |

FOREIGN PATENT DOCUMENTS

| | | |
|---|---|---|
| 0242100 | 10/1987 | (EP) . |
| 0246828 | 11/1987 | (EP) . |
| 0322812 | 7/1989 | (EP) . |
| 0491075 | 6/1992 | (EP) . |
| 0592309 | 4/1994 | (EP) . |
| 90/14447 | 11/1990 | (WO) . |
| 95/26169 | 10/1995 | (WO) . |

OTHER PUBLICATIONS

H. W. Bergmann, "Thermochemische Behandling von Titan und Titanlegierungen durch Laserumschmelzen und Gaslegieren", Zeitschrift für Werkstofftechnik 16 pp. 392–405 (1985). (No Month).

A. Kolitsch et al., "Modification of Laser–Arc DLC Layers by Ion Beams" Proceedings. International Symposium Trends New Applications on Thin Films, (Jan. 1, 1993).

WEAR-RESISTANCE EDGE LAYER STRUCTURE FOR TITANIUM OR ITS ALLOYS WHICH CAN BE SUBJECTED TO A HIGH MECHANICAL LOAD AND HAS A LOW COEFFICIENT OF FRICTION, AND METHOD OF PRODUCING THE SAME

BACKGROUND

1. Field of the Invention

The invention concerns edge layer refinement of functional components. The present invention is useful in all functional components subjected to wear caused by sliding friction made of titanium or its alloys, which are stressed at operating temperatures below 500° C., are subjected to high surface pressure, and must have as low a coefficient of friction as possible. The invention can be used particularly advantageously for the protection of human implants, in particular with oscillating movements, as well as aerospace sector components subjected to wear caused by sliding friction.

2. Discussion of Background

Titanium is an excellent construction material whose high specific strength, chemical resistance, and biocompatibility make titanium suitable for various special applications. However, titanium's low resistance to wear caused by sliding friction and its high coefficient of friction often prevent a broader range of use.

It is known to produce very wear-resistant edge layers on titanium by laser gas alloying (cf., e.g., H.W. Bergmann: "Thermochemical Treatment of Titanium and Titanium Alloys by Laser Melting and Gas Alloying", Zeitschrift für Werkstofftechnik 16 (1985), p. 392–405).

Moreover, it is known to use laser gas alloying for the protection of joint endoprostheses (DE 3 917 211). For this, the component is melted by the laser beam to a depth of 0.1 to 0.7 mm, and nitrogen is simultaneously blown into the melt. Because of the high affinity of titanium for reactive gases, titanium nitride, which precipitates in the form of needles from the melt, forms immediately. After solidification, the edge layer consists of the metallic matrix of titanium with an altered $\alpha/\beta$ proportion compared to the initial state, as well as very densely embedded titanium nitride needles. The hardness of the edge layer is usually up to 1000 HV.

However, the shortcoming of such layers include a high coefficient of friction and, moreover, strong abrasive wear with most mating bodies which may be used. In this regard, the very hard titanium nitride needles protrude out of the surface after the initial wear. Thus, the local stress of the tribosystem is increased until the mating body is grooved and simultaneously microscopic interlocking of the titanium nitride needles with the mating body results, which increases the coefficient of friction.

Another shortcoming of these layers appears under loading in an oxygen-containing atmosphere and especially under relatively high temperatures and is expressed in that, particularly under deficient lubrication conditions, a catastrophic failure of the frictional pair may occur. The cause for this failure involves the metallic matrix between the TiN needles havings a high affinity for oxygen.

In order to circumvent the negative effects of the TiN needles, in particular for the human implant sector, a process for gas nitriding (U.S. Pat. No. 5,326,362) has become known in which molecular nitrogen is diffused into the region near the surface at a process temperature of 400° C. to 704.4° C. and forms a wear-resistant layer by solution hardening. For this, the component is placed in a vacuum furnace, evacuated to a pressure of $1 \cdot 10^{-6}$ Torr, then filled with 1 atm nitrogen, heated to 537.7° C.; the nitrogen pressure is increased to 2 atm, and the component is nitrided at 593.3° C. for several hours. After completion of the treatment, the edge layer comprises a 0.2 $\mu$m-thick compound layer of titanium nitrides, titanium carbon nitrides, titanium oxides, and titanium carbo-oxides and a diffusion layer a few $\mu$m thick. The titanium nitrides found in the compound layer are significantly more finely dispersed than with laser gas alloying. Since the compound layer forms a closed layer on the surface, the loading capacity of the layer under an oxygen-containing atmosphere and elevated temperatures is increased.

The shortcomings of this process include that the friction coefficient is not adequately reduced and that the wear resistance is inadequate at high contact pressures. The shortcomings result from the fact that, on the one hand, the compound layer still comprises a very hard and not completely flat titanium nitride needles, which interlock with the mating body and, on the other hand, the underlying diffusion layer is too thin to be able to resist high local stress for an adequately long time. The primary reason for the latter is that with Hertz-calculated stresses with the contact surfaces appearing in actual practice, the maximum stress lies under the layer. Consequently, deformations may occur in the soft base material, which result in a lifting of the brittle compound layer.

SUMMARY OF THE INVENTION

An object of an invention is to provide a biocompatible edge layer structure which is resistant to wear caused by sliding and with a very low sliding friction coefficient for titanium and its alloys and to propose a process for its production.

Another object of the invention is to provide an edge layer structure which has a greater hardness penetration depth by at least one order of magnitude by making use of the high wear resistance of titanium nitride and which contains no titanium nitride needles directly in its surface.

The invention is directed to a wear-resistant, mechanically highly stressable, low friction edge layer structure for titanium or its alloys, consisting of a laser gas alloyed layer with precipitated titanium nitride needles.

The present invention is also directed to an intermediate layer, with which a particularly good adhesion of the hard alorphous carbon layer is achieved.

In addition, the present invention involves a process for production of an edge layer structure with a low coefficient of friction and a very high load carrying capacity.

In accordance with one aspect, the present invention is directed to a wear-resistant edge layer for titanium and its alloys which can be subjected to high loads and has a low coefficient of friction, comprising: a hard amorphous carbon layer; an intermediate layer; and a laser gas alloyed layer.

In accordance with another aspect, the present invention is directed to a wear-resistant edge layer for titanium and its alloys which can be subjected to high loads and has a low coefficient of friction, comprising: 200 to 400 nm thick hard amorphous carbon layer; 50 to 200 nm thick intermediate layer; and 0.3 to 2.0 mm thick laser gas alloyed layer, the laser gas alloyed layer comprising precipitated titanium nitride needles and having a hardness between 600 HV0.1 and 1400 HV0.1.

The intermediate layer may comprise titanium or may consist of titanium.

In another aspect, the present invention is directed to a process for producing a wear resistant edge layer on a substrate, comprising: forming a laser gas alloyed layer by melting a surface of a substrate; applying an intermediate layer by Laser-Arc; and depositing a hard amorphous carbon layer on the intermediate layer by Laser-Arc.

In another aspect, the present invention is directed to a process for producing a wear-resistant edge layer on a substrate, comprising: forming a laser gas alloyed layer by melting tracks in a substrate surface with a high power laser, the high power laser having a power density of $1 \cdot 10^4$ W/cm² to $2 \cdot 10^5$ W/cm², the melting taking place in a reactive atmosphere having an oxygen partial pressure less than 5 ppm, the reactive atmosphere comprising $N_2$ and Ar wherein a nitrogen content is 40% to 80%, an overlap level Ü being 0.5 to 0.9 where Ü=(a−c)/a and where a is a track width and c is a track spacing; after melting the tracks, polishing the substrate to a surface roughness less than or equal to 0.2 μm; cleaning the substrate with a high vacuum device by ion bombardment; after cleaning the substrate, applying an intermediate layer by Laser-Arc; and after application of the intermediate layer, depositing a hard amoi-phouts carbon layer on the intermediate layer by Laser-Arc.

In one aspect, the application of the intermediate layer by Laser-Arc comprises a laser controlled, pulsed vacuum arc.

In another aspect, the deposition of the hard amorphous carbon layer by Laser-Arc comprises a laser controlled, pulsed vacuum arc.

In still another aspect, the application of the intermediate layer by Laser-Arc and the deposition of the hard amorphous carbon layer by Laser-Arc are performed with a same arrangement.

BRIEF DESCRIPTION OF THE DRAWINGS

The associated drawings depict the layer structure (FIG. 1) according to the invention and the improvement in wear behavior (FIG. 2a) and friction behavior (FIG. 2b).

DETAILED DESCRIPTION

Figure 1:
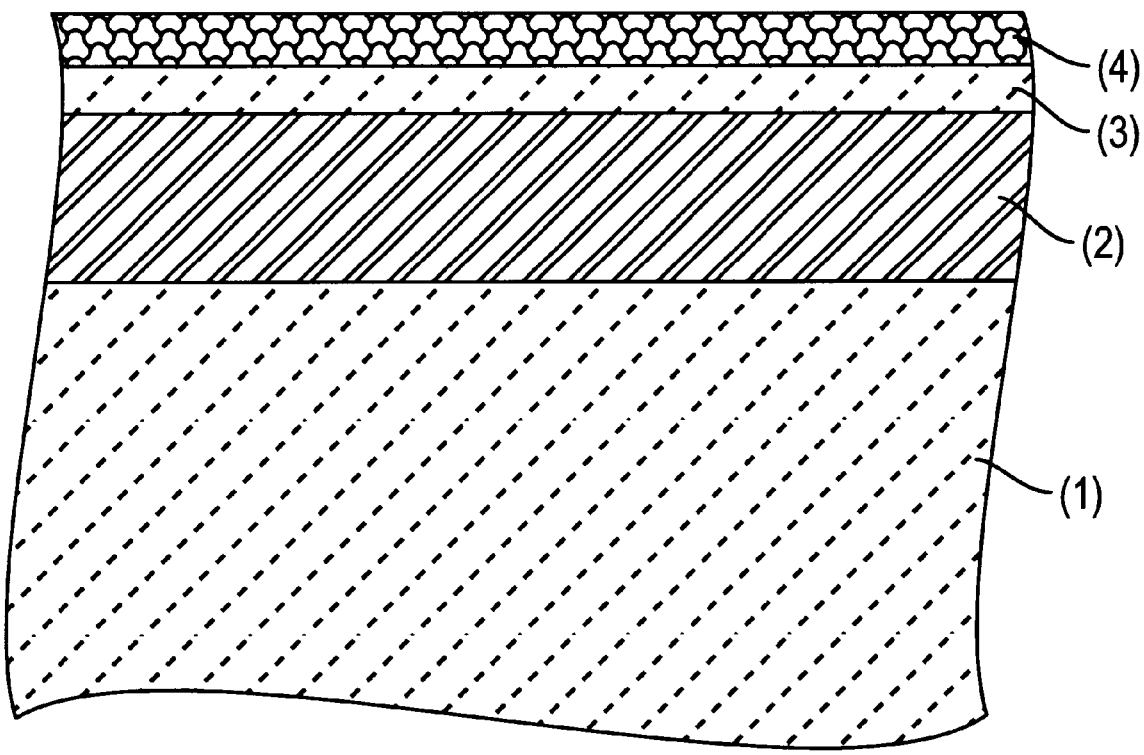
Figure 2A:
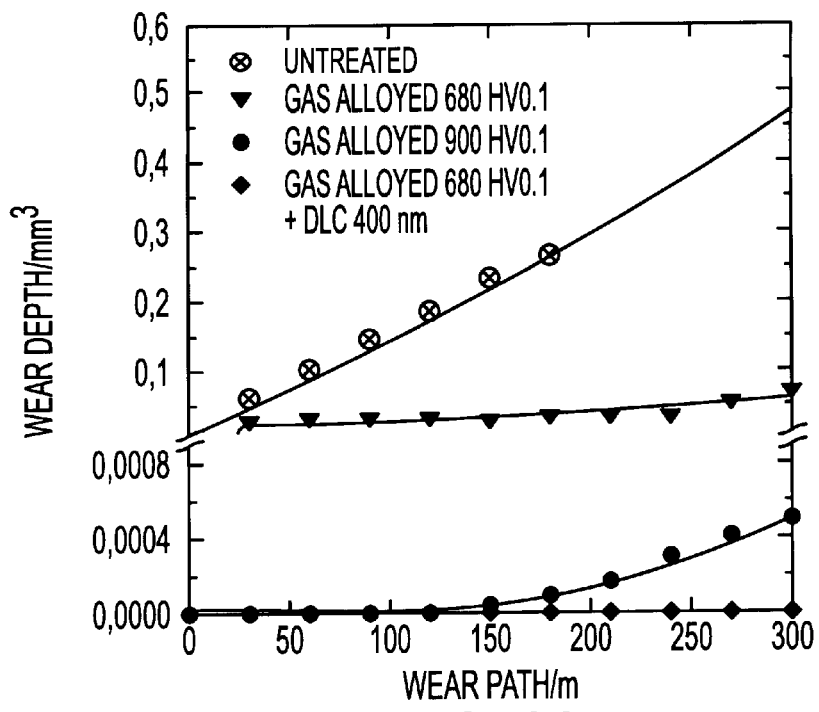
Figure 2B:
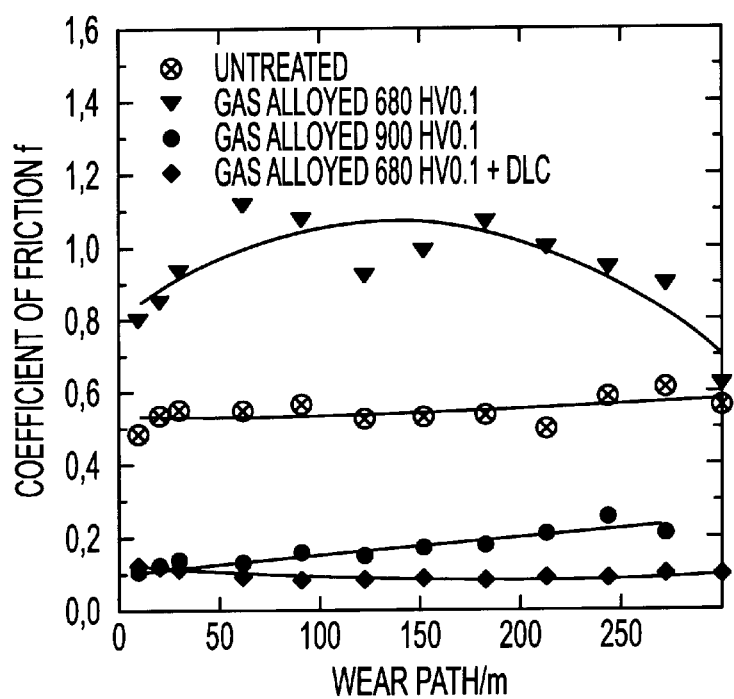

The invention is explained in detail with reference to the following exemplary embodiment.

EXAMPLE 1

A component 1 made of the alloy Ti6A14V with the dimensions 10×40×60 mm³ was provided on a flat side with a very wear-resistant and low friction layer structure.

For this, the component 1, polished and cleaned of fatty residues by a solvent, was positioned on the work table of a CNC machine. A special bell-shaped shielding Gas attachment, into which an $N_2$/Ar mixture at atmospheric pressure adjusted in a gas mixing station at the ratio $N_2$:Ar=60:40 or $N_2$:Ar=70:30 was blown in, was placed above the component. The bell-shaped shielding attachment was designed such that it was freely movable in three coordinate directions, and after a 90-sec scavenging period, a residual oxygen content ≦3 ppm was guaranteed. The laser power was 5 kW; the beam had a diameter of 3.4 mm on the component; the feed rate was selected at 8 mm/s. The track spacing was 0.75 mm with a resultant track width of 4.5 mm. This yielded an overlap level of 83.3%. After reaching the oxygen partial pressure <5 ppm, the process of gas alloying was initiated by starting the CNC program and releasing the laser beam. The gas alloyed layer 2 thus produced was 1.2 mm deep, comprising titanium nitride needles, which were embedded in a titanium matrix.

After cooling of the component, its surface was polished with a diamond grinding wheel with a grain size of 125 μm until a uniform surface with a roughness ≦0.62 μm was obtained. This is followed by grinding with SiC paper P800 to P1200, until a roughness ≦0.12 μm was obtained.

Then, the surface of the component was cleaned in a vacuum chamber by ion bombardment with argon ions. In the same chamber, there was an arrangement for performance of the laser controlled, pulsed vacuum arc process (laser arc process) to produce a hard amorphous carbon layer. The arrangement includes a pulsed vacuum arc, the target material connected as the cathode as well as a Q-switched Nd-YAG laser with a power density >$5 \cdot 10^8$ W/cm². The component was fastened in a substrate holder.

The cylindrical cathode is bipartite, comprising a titanium and a graphite cylinder.

A voltage inadequate to cause an arc discharge was applied between the cathode and the anode. The laser was focused on the titanium cylinder and turned on. Its pulses generated plasma clouds, each of which caused a brief were discharge. Ti ions and atoms are deposited on the substrate. After reaching the desired layer thickness of the intermediate layer 3, a switch was made to the graphite cathode, and the hard amorphous carbon layer 4 was deposited on the component. The layer deposited was 400 mm thick and comprised a hard amorphous carbon film.

To determine wear resistance, the components were tested on a ball-on-disk tribometer, wherein the ball was made of hard metal.

What is claimed is:

1. A wear-resistant edge layer for titanium and its alloys which can be subjected to high loads and has a low coefficient of friction, comprising:

a hard amorphous carbon layer;

an intermediate layer; and a laser gas alloyed layer.

2. The wear-resistant edge layer of claim 1, wherein the hard amorphous carbon layer is 200 to 400 nm thick.

3. The wear-resistant edge layer of claim 1, wherein the intermediate layer is 50 to 200 nm thick.

4. The wear-resistant edge layer of claim 1, wherein the laser gas alloyed layer is 0.3 to 2.0 mm thick.

5. The wear-resistant edge layer of claim 1, wherein the laser gas alloyed layer comprises precipitated titanium nitride needles.

6. The wear-resistant edge layer of claim 1, wherein the laser gas alloyed layer has a hardness between 600 HV0.1 and 1400 HV0.1.

7. The wear-resistant edge layer of claim 1, wherein the intermediate layer comprises titanium.

8. The wear-resistant edge layer of claim 1, wherein the intermediate layer consists of titanium.

9. A wear-resistant edge layer for titanium and its alloys which can be subjected to high loads and has a low coefficient of friction, comprising:

200 to 400 nm thick hard amorphous carbon layer;

50 to 200 nm thick intermediate layer; and 0.3 to 2.0 mm thick laser gas alloyed layer, the laser gas alloyed layer comprising precipitated titanium nitride needles and having a hardness between 600 HV0.1 and 1400 HV0.1.

10. The wear-resistant edge layer of claim 9, wherein the intermediate layer comprises titanium.

11. The wear-resistant edge layer of claim 9, wherein the intermediate layer consists of titanium.

12. A wear-resistant component which can be subjected to high loads and has a low coefficient of friction, comprising:
   a hard amorphous carbon layer;
   an intermediate layer;
   a laser gas alloyed layer; and
   a substrate comprised of titanium.

13. A process for producing a wear resistant edge layer on a substrate, comprising:
   forming a laser gas alloyed layer by melting a surface of a substrate;
   applying an intermediate layer by Laser-Arc; and
   depositing a hard amorphous carbon layer on the intermediate layer by Laser-Arc.

14. The process of claim 11, wherein the substrate comprises one of titanium and titanium alloy.

15. The process of claim 13, wherein foiling the laser gas alloyed layer comprises melting tracks in the surface of the substrate with a laser, the melting taking place in a reactive atmosphere comprising $N_2$ and Ar.

16. The process of claim 15, wherein the laser has a power density of $1 \cdot 10^4$ W/cm$^2$ to $2 \cdot 10^5$ W/cm$^2$.

17. The process of claim 15, wherein the reactive atmosphere has an oxygen partial pressure less than 5 ppm.

18. The process of claim 15, wherein the reactive atmosphere has a nitrogen content of 40% to 80%.

19. The process of claim 15, wherein an overlap level $\ddot{U}$ is 0.5 to 0.9 where $\ddot{U}=(a-c)/a$ and where a is a track width and c is a track spacing.

20. The process of claim 13, further comprising after melting the surface of the substrate, polishing the substrate to a surface roughness less than or equal to 0.2 $\mu$m.

21. The process of claim 13, further comprising cleaning the substrate with a high vacuum device by ion bombardment.

22. The process of claim 13, wherein applying the intermediate layer is by Laser-Arc.

23. The process of claim 22, wherein the Laser-Arc comprises a laser controlled, pulsed vacuum arc.

24. The process of claim 13, wherein depositing the hard amorphous carbon layer is by Laser-Arc.

25. The process of claim 24, wherein the Laser-Arc comprises a laser controlled, pulsed vacuum arc.

26. The process of claim 13, wherein applying the intermediate layer and depositing the hard amorphous carbon layer are by Laser-Arc in a same arrangement.

27. The process of claim 13, wherein the wear-resistant edge layer comprises:
   a hard amorphous carbon layer;
   an intermediate; and
   a laser gas alloyed layer.

28. The process of claim 13, wherein the wear-resistant edge layer comprises:
   200 to 400 nm thick hard amorphous carbon layer;
   50 to 200 nm thick intermediate layer; and
   0.3 to 2.0 mm thick laser gas alloyed layer, the laser gas alloyed layer comprising precipitated titanium nitride needles and having a hardness between 600 HV0.1 and 1400 HV0.1.

29. A process for producing a wear-resistant edge layer on a substrate, comprising:
   forming a laser gas alloyed layer by melting tracks in a substrate surface with a high power laser, the high power laser having a power density of $1 \cdot 10^4$ W/cm$^2$ to $2 \cdot 10^5$ W/cm$^2$, the melting taking place in a reactive atmosphere having an oxygen partial pressure less than 5 ppm, the reactive atmosphere comprising $N_2$ and Ar wherein a nitrogen content is 40% to 80%, an overlap level $\ddot{U}$ being 0.5 to 0.9 where $\ddot{U}(a-c)/a$ and where a is a track width and c is a track spacing;
   after melting the tracks, polishing the substrate to a surface roughness less than or equal to 0.2 $\mu$m;
   cleaning the substrate with a high vacuum device by ion bombardment;
   after cleaning the substrate, applying an intermediate layer by Laser-Arc; and
   after application of the intermediate layer, depositing a hard amorphous carbon layer on the intermediate layer by Laser-Arc.

30. The process of claim 29, wherein the substrate comprises one of titanium and tutanium alloy.

31. The process of claim 29, wherein the application of the intermediate layer by Laser-Arc comprises a laser controlled, pulsed vacuum arc.

32. The process of claim 29, wherein the deposition of the hard amorphous carbon layer by Laser-Arc comprises a laser controlled, pulsed vacuum arc.

33. The process of claim 29, wherein the application of the intermediate layer by Laser-Arc and the deposition of the hard amorphous carbon layer by Laser-Arc are performed with a same arrangement.

34. The process of claim 29, wherein the wear-resistant edge layer comprises:
   a hard amorphous carbon layer;
   an intermediate layer; and
   a laser gas alloyed layer.

35. The process of claim 29, wherein the wear-resistant edge layer comprises:
   200 to 400 nm thick hard amorphous carbon layer;
   50 to 200 nm thick intermediate layer; and
   0.3 to 2.0 mm thick laser gas alloyed layer, the laser gas alloyed layer comprising precipitated titanium nitride needles and having a hardness between 600 HV0.1 and 1400 HV0.1.

* * * * *